US00PP31670P2

(12) United States Plant Patent
Klemm et al.

(10) Patent No.: US PP31,670 P2
(45) Date of Patent: Apr. 14, 2020

(54) POINSETTIA PLANT NAMED 'NPCW18289'

(50) Latin Name: *Euphorbia pulcherrima*
Varietal Denomination: NPCW18289

(71) Applicant: Klemm+Sohn GmbH & Co. KG, Stuttgart (DE)

(72) Inventors: Nils Klemm, Stuttgart (DE); Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/501,253

(22) Filed: Mar. 12, 2019

(51) Int. Cl.
*A01H 5/02* (2018.01)
*A01H 6/38* (2018.01)

(52) U.S. Cl.
USPC ..... Plt./303

(58) Field of Classification Search
USPC ..... Plt./303
CPC ..... A01H 5/02; A01H 5/0244; A01H 6/38; A01H 6/385
See application file for complete search history.

(56) References Cited

PUBLICATIONS

Harris Seeds 2018 Poinsettia Liners Grown by Raker-Roberta's, Michigan, retrieved on Nov. 6, 2019, retrieved from the Internet at https://cdn.shopify.com/s/files/1/1537/5553/files/RakerPoinsettiaProgram.pdf, cover page, pp. 1-4 (Year: 2018).*
Select One Series Information 2019, retrieved on Nov. 6, 2019, retrieved from the Internet at http://www.selectanorthamerica.com/series_info.aspx?phid=050006473004304#, one page. (Year: 2019).*

* cited by examiner

*Primary Examiner* — June Hwu
(74) *Attorney, Agent, or Firm* — Barbara Campbell; James M. Weatherly; Cochran Freund & Young LLC

(57) ABSTRACT

A new poinsettia plant particularly distinguished by having speckled and marbled bracts, and excellent keeping quality is disclosed.

1 Drawing Sheet

Genus and species: *Euphorbia pulcherrima.*
Variety denomination: 'NPCW18289'.

BACKGROUND OF THE NEW PLANT

The present invention comprises a new and distinct variety of poinsettia, botanically known as *Euphorbia pulcherrima* and hereinafter referred to by the variety name 'NPCW18289'. 'NPCW18289' was derived from an irradiated cutting of the Poinsettia variety CHRISTMAS BEAUTY Red, (also known as 'NPCW10158' U.S. Plant Pat. No. 22,580), having red bracts, in April 2014 in a green house in Stuttgart, Germany.

In November 2014, a single plant was selected in Stuttgart, Germany. In February 2015, 'NPCW18289' was first asexually propagated by apical cuttings. 'NPCW18289' was found to reproduce true to type in successive generations of asexual propagation via vegetative apical cuttings in Stuttgart, Germany.

SUMMARY

The following are the most outstanding and distinguishing characteristics of this new variety when grown under normal horticultural practices in Stuttgart, Germany.

1. Speckled and marbled bracts; and
2. Excellent keeping quality.

DESCRIPTION OF THE PHOTOGRAPH

This new poinsettia plant is illustrated by the accompanying photograph which shows an overall view of the whole plant. The photograph is of a plant approximately 12 weeks old grown indoors in Stuttgart, Germany in December 2016. The colors shown are as true as can be reasonably obtained by conventional photographic procedures.

DESCRIPTION OF THE NEW VARIETY

The following detailed descriptions set forth the distinctive characteristics of 'NPCW18289'. The data which define these characteristics were collected from asexual reproductions carried out in Stuttgart, Germany. Data was collected on plants aged approximately 18 weeks-old after potting and grown in a glass greenhouse in Stuttgart, Germany in December 2018. Color references are to The R.H.S. Colour Chart of The Royal Horticultural Society of London (R.H.S.), 5$^{th}$ edition (2007) unless where otherwise stated.

Classification:
*Family.*—Euphorbiaceae.
*Species.*—*Euphorbia pulcherrima.*
*Common name.*—Poinsettia.
*Variety.*—'NPCW18289'.

Parentage: CHRISTMAS BEAUTY Red, (also known as 'NPCW10158' U.S. Plant Pat. No. 22,580).

Growth:
*Blooming habit.*—Intermittent.
*Flowering response time.*—Approximately 60 days.
*Keeping quality.*—Excellent.

Plant description:
*Form.*—Triangular.
*Growth habit.*—Upright.
*Height.*—25.0 cm to 28.0 cm.

*Width.*—25.0 cm to 38.0 cm.
*Average number of inflorescences per plant.*—7.

Propagation:
*Type cuttings.*—Apical cuttings.
*Time to produce a rooted cutting.*—4 weeks.
*Rooting habit and root color.*—Freely branching and white.

Lateral branches:
*Color.*—RHS 143A.
*Length.*—23.0 cm.
*Internode length.*—1.0 cm to 3.0 cm.
*Diameter.*—0.5 cm to 0.8 cm.
*Branching habit.*—Freely branching.
*Number of lateral branches per plant.*—6 to 8.
*Texture.*—Smooth.
*Strength.*—Medium.

Leaves:
*Quantity.*—6 to 7 per lateral branch.
*Arrangement.*—Alternate.
*Number of lobes on the leaf blade.*—Varies from 0 to 6 (most leaves without lobes).
*Lobation depth.*—Shallow.
*Depth of the deepest sinus of the leaf blade.*—0.3 cm to 0.5 cm.
*Shape.*—Ovate.
*Apex.*—Acute.
*Base.*—Obtuse.
*Margin.*—Mostly entire (only a few leaves per plant that are serrate).
*Length.*—6.0 cm to 11.0 cm.
*Width.*—5.0 cm to 8.0 cm.
*Texture (both surfaces).*—Smooth.
*Vein color.*—Upper surface: RHS 142C. Lower surface: RHS 142C.
*Venation pattern.*—Reticulate.
*Variegation.*—Absent.
*Color.*—Mature foliage: Upper surface: RHS 139A. Lower surface: RHS 138B. Immature foliage: Upper surface: RHS 141A. Lower surface: RHS 138A.
*Leaf petiole.*—Length: 2.5 cm to 5.0 cm. Diameter: 0.2 cm to 0.3 cm. Color: Upper (part) surface: RHS 143C with reddish spots (RHS 181A). Lower (part) surface: RHS 143C. Texture: Smooth. Strength: Medium.
*Transitional leaves.*—Few in number, leaf shape is ovate, the central part of the bracts, which has the lighter color, is a bit greenish on the transitional bracts, whereas the outer part has a pale reddish appearance, length is 5 cm to 8 cm, width is 3 cm to 5 cm, and lobing is absent; the central part of the bracts, which has the lighter color, is a bit greenish on the transitional bracts, whereas the outer part has a pale reddish appearance; the shape is ovate.

Inflorescence:
*Type and habit.*—Cluster of cyathia.
*Quantity per lateral branch.*—1 compound of cyathias accompanied by bracts.
*Position relative to foliar plane.*—Above.
*Lastingness of inflorescence on the plant.*—4 weeks.
*Natural flowering season.*—End of November.
*Diameter.*—15.0 cm to 20.0 cm.
*Height.*—2.0 cm to 3.0 cm.
*Fragrance.*—Absent.

Bracts:
*Number of bracts per inflorescence.*—6 to 8.
*Lobing.*—Absent.
*Rugosity between the veins.*—Absent.
*Twisting.*—Absent.
*Shape.*—Ovate.
*Apex.*—Acute.
*Base.*—Obtuse.
*Margin.*—Entire.
*Size.*—Length: 6.0 cm to 9.0 cm. Width: 3.0 cm to 6.0 cm. Texture (both upper and lower surfaces): Smooth.
*Venation pattern.*—Reticulate.
*Vein color.*—Upper surface: RHS 140B with the smaller veins described as transparent. Lower surface: RHS 140B.
*Bract color.*—Upper surface: There are two color patterns. Primary pattern: marbling between a more reddish outer part and a more whitish/yellowish central part. The bracts in general are colored RHS 5D with RHS 46B spots. The spots condense to plain RHS 46B towards the margins. Secondary pattern: spotting of 46B on RHS 5D background in the central part. Lower surface: There are two color patterns. Primary pattern: marbling between a more reddish outer part and a more whitish/yellowish central part. The bracts in general are colored RHS 5D with RHS 47B spots. The spots condense to plain RHS 47B towards the margins. Secondary pattern: spotting of 47B on RHS 5D background in the central part.
*Bract petiole.*—Length: 0.5 cm to 2.0 cm. Diameter: 0.2 cm to 0.3 cm. Color: Upper (part) surface: RHS 140B. Lower (part) surface: RHS 140B. Texture: Smooth. Strength: Medium.

Cyme:
*Diameter.*—1.0 cm to 2.0 cm.
*Cyathia number.*—6 to 9 per inflorescence.
*Deformation of glands of the cyathium.*—Absent.
*Timing of opening of cyathia.*—Beginning of November. First pollen appears in parallel to opening of the nectar cups; stigmas appear 2 weeks later.
*Cyathium.*—Shape: Ovate. Texture (inner and outer surfaces): Smooth. Diameter: 0.2 cm to 0.5 cm. Length: 0.2 cm to 0.7 cm. Color: RHS 143C.
*Peduncle.*—Color: RHS 142B. Length: 0.2 cm. Diameter: 0.1 cm. Texture: Smooth. Strength: Medium.
*Nectar cups.*—Number: 1 per cyathium. Diameter: 0.1 cm. Length: 0.4 cm to 0.5 cm. Color: RHS 21B. Shape: Lip-shaped. Texture (inner and outer surfaces): Smooth.

Fruit and seed set: None observed.

Disease and pest resistance: No special disease or pest resistance observed.

COMPARISON WITH PARENTAL AND KNOWN VARIETY

'NPCW18289' is a distinct variety of poinsettia. 'NPCW18289' differs from the parental line CHRISTMAS BEAUTY Red in that CHRISTMAS BEAUTY Red has red bracts colored RHS 45B whereas 'NPCW18289' has bracts colored RHS 5D with RHS 46B spots (bracts that are marbling between a more reddish outer part and a more whitish/yellowish central part).

'NPCW18289' is distinguished from commercial line 'Premium Ice Crystal' (unpatented) as shown below in Table 1.

TABLE 1

| Characteristic | 'NPCW18289' | 'Premium Ice Crystal' |
|---|---|---|
| Bract size | Small to Medium | Large |
| Leaf size | Medium | Large |
| Response time | Minimum 60 days | Less than 55 days |

We claim:

1. A new and distinct variety of poinsettia plant designated 'NPCW18289' as illustrated and described herein.

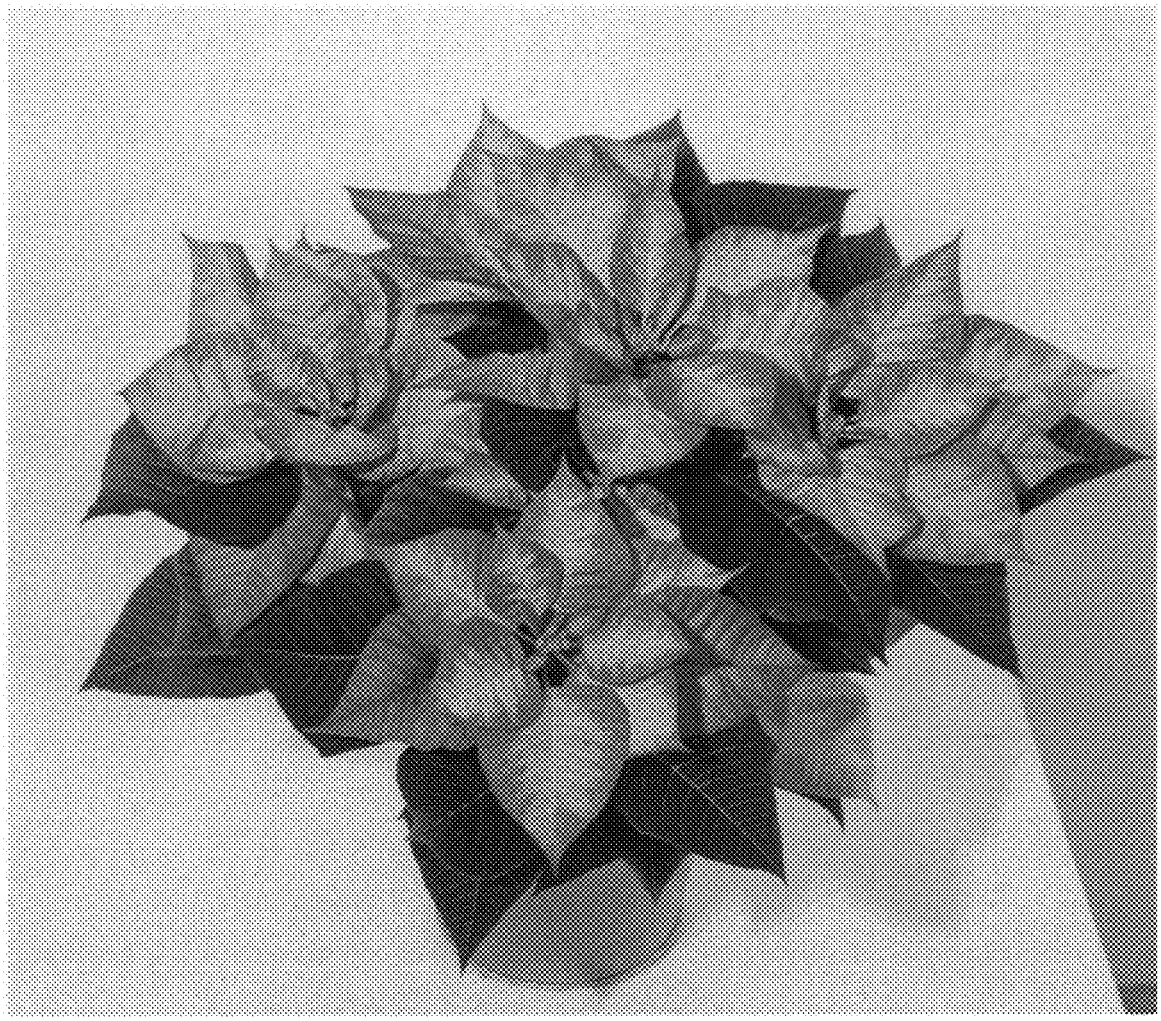

* * * * *